United States Patent [19]

Guigan

[11] 4,412,973

[45] Nov. 1, 1983

[54] AUTONOMOUS SIMULTANEOUS ANALYSIS APPARATUS AND A METHOD OF USING IT

[76] Inventor: Jean Guigan, 9, rue Jean Mermoz, 75008 Paris, France

[21] Appl. No.: 330,430

[22] Filed: Dec. 14, 1981

[30] Foreign Application Priority Data

Dec. 15, 1980 [FR] France ................................ 80 26528

[51] Int. Cl.³ ...................... G01N 21/07; G01N 33/54
[52] U.S. Cl. ......................................... 422/72; 494/16; 356/246; 422/102; 422/61; 422/104; 436/45
[58] Field of Search ................. 422/72, 102, 101, 104, 422/64, 61; 233/26; 356/244, 246; 436/45

[56] References Cited

U.S. PATENT DOCUMENTS

| | | | |
|---|---|---|---|
| 4,244,694 | 1/1981 | Farina et al. ........................... | 422/72 |
| 4,244,916 | 1/1981 | Guigan .................................. | 422/72 |
| 4,279,862 | 7/1981 | Bretaudiere ........................... | 422/72 |
| 4,284,602 | 8/1981 | Kelton et al. .......................... | 422/72 |
| 4,314,968 | 2/1982 | Guigan .................................. | 422/72 |

FOREIGN PATENT DOCUMENTS 468478 10/1972 Australia ............................... 422/72

*Primary Examiner*—Michael S. Marcus
*Attorney, Agent, or Firm*—Sughrue, Mion, Zinn, Macpeak and Seas

[57] ABSTRACT

Analysis apparatus which uses a solid reaction support designed to hold successively a quantity of a compound such as a biological liquid which contains a substance to be analyzed, and then a quantity of a first reagent on which is fixed a biological indicator. The apparatus is constituted by an analysis rotor (1) which includes a plurality of peripheral reaction cells (2) each of which contains said reaction support (3), said cells being provided with a peripheral liquid-removal orifice (7). Means (4, 5) convey a washing liquid towards each reaction cell. Each of said reaction cells (2) is associated with a buffer cell (10), which successively receives at least the compound and the first reagent. It shares a common wall (11) with the reaction cell (2). A passage (25) is provided between the cells of each pair through said common wall (11). The first reagent is contained in a suitable receptacle (14) supported by the analysis apparatus. Means are provided to open said receptacle (14) to pour the reagent into the buffer cell (10).

14 Claims, 14 Drawing Figures

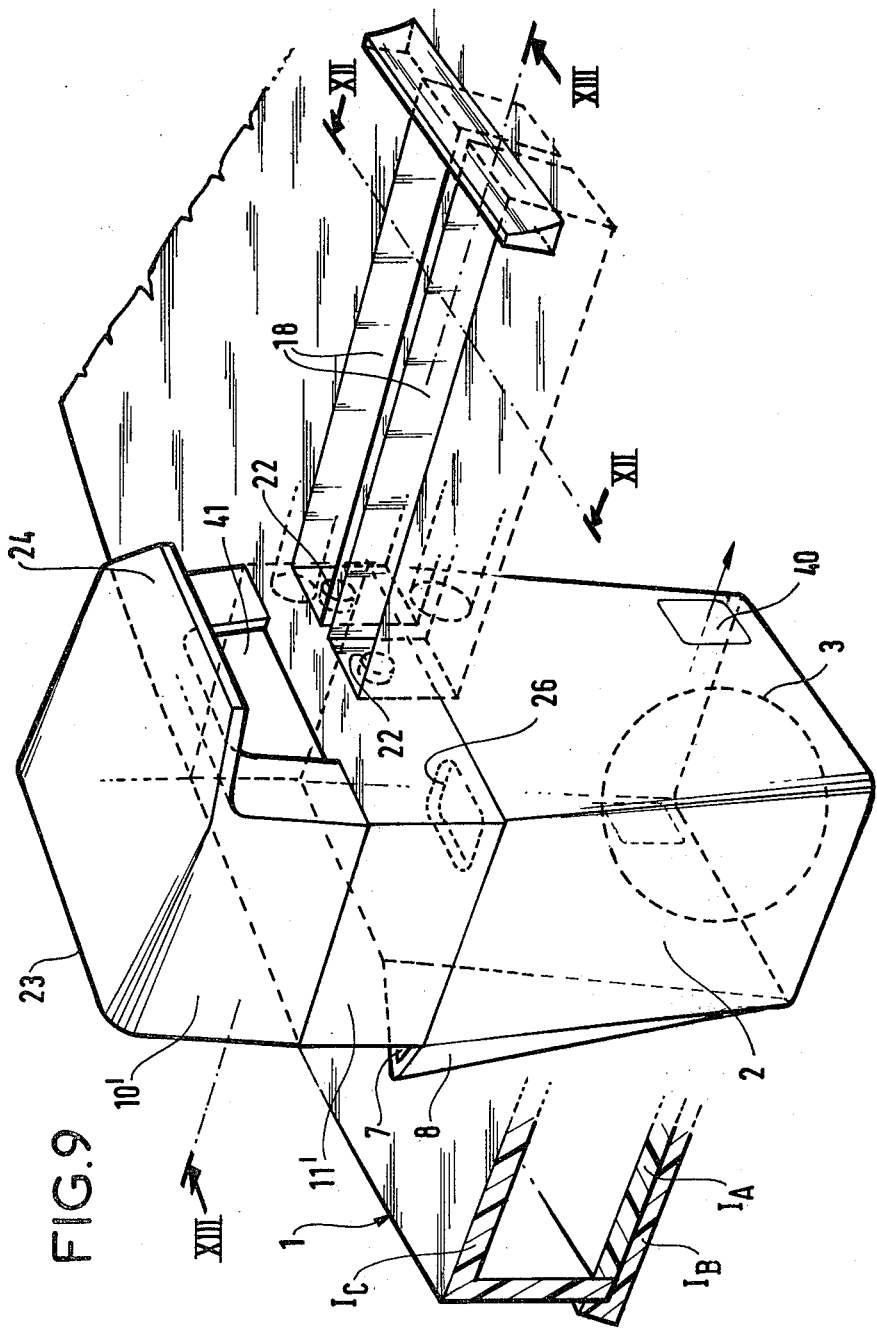

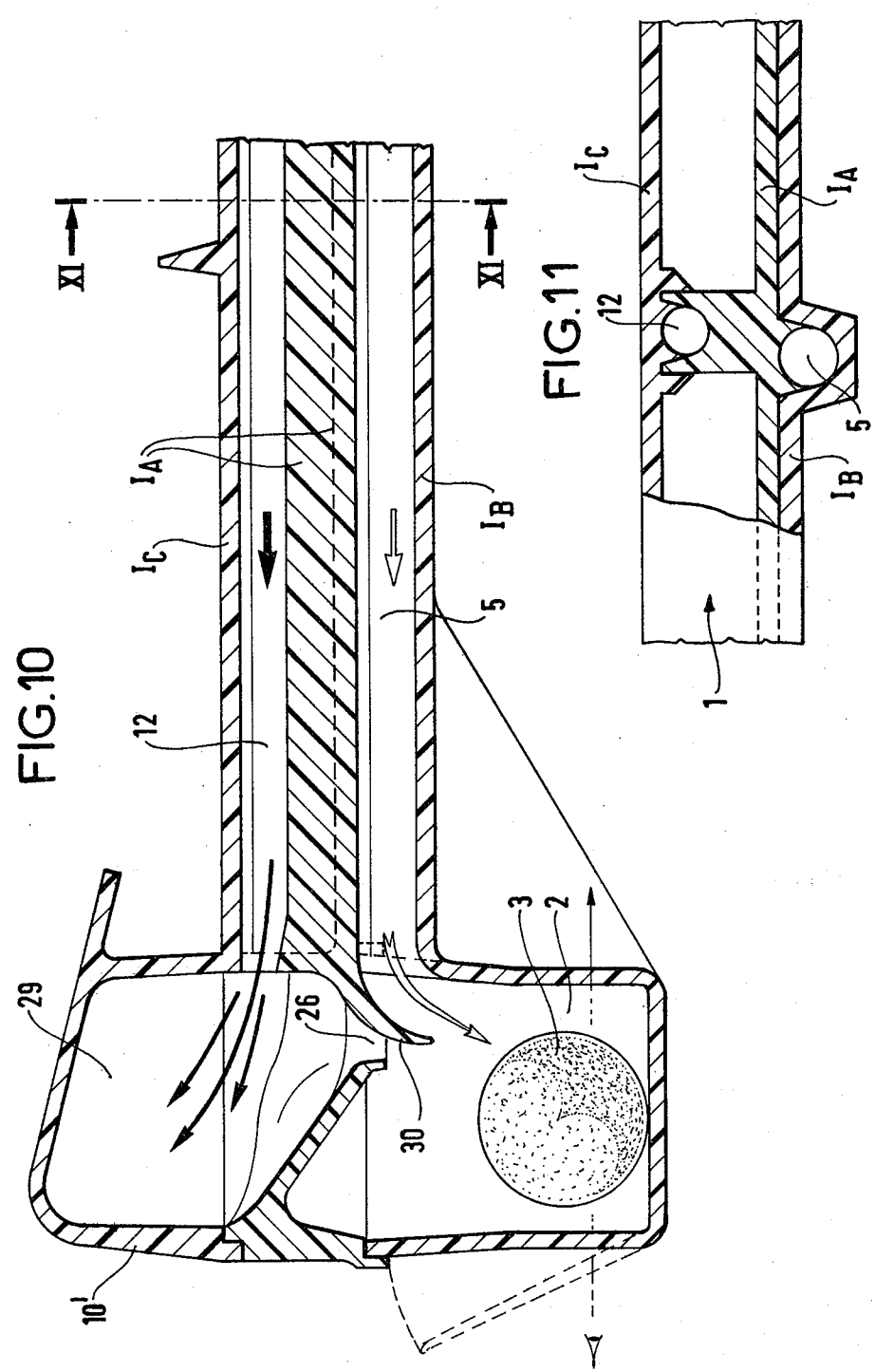

AUTONOMOUS SIMULTANEOUS ANALYSIS APPARATUS AND A METHOD OF USING IT

The invention relates to analysis apparatus of the kind which uses a reaction support to hold successively a quantity of a liquid which contains a substance to be analysed and then a quantity of a liquid reagent to react therewith.

BACKGROUND OF THE INVENTION

Present techniques use a solid support which is usually a spherical polystyrene bead covered with a protein (e.g. a polypeptide coming from a vaccinated animal) which has anti-body type properties. In prior art apparatus, said support is disposed in a test tube type receptacle into which the compound containing the substance to be analysed is admitted and, after a suitable incubation period, the bead must be thoroughly washed with water to remove the excess compound. Said washing is manual as is the removal of the liquid, the tube being turned upside down and the open end of the tube having tabs which prevent the bead from falling out. The operation must then be repeated with the reagent, and its excess is again removed by washing, after which the tube is conveyed to an analysis unit proper e.g. for photocolorimetric analysis by injecting a suitable coloured reagent.

Although the principle of the support bead which successively holds the compound and the reagent is very simple and effective, the technique used gives little satisfaction: indeed, the washing operations carried out by hand are not very reliable because washes and temperature conditions differ on different occasions, and they are unsuitable for analyses using grouped tests with different dosages because of the numerous handling operations which are necessary.

That is why U.S. patent application No. 198,323 discloses a more reliable apparatus of simple design and perfectly suited to simultaneous analysis using general dosages and a minimum of handling.

This apparatus is constituted by an analysis rotor which has a plurality of peripheral cells each of which contains a reaction support together with means to convey washing liquid to each cell, each of said cells being provided with a peripheral liquid-removal orifice and having an upper portion provided with an inlet orifice for a compound and a reagent.

The means which allow the washing liquid to be conveyed are constituted in the main by a central inlet orifice from which radial pipes leave to connect said central orifice to each of the peripheral cells; preferably, the radial pipes are in a plane which is essentially perpendicular to the axis of rotation of the apparatus.

Such apparatus operates as follows:

The rotor is disposed beneath a feed device so as to inject a calibrated volume of compound such as serum, plasma or any other biological liquid which contains the substance to be analysed into each cell via an upper orifice, after this injection the compound is allowed to rest during the necessary incubation time.

The rotor is then set in motion and washing liquid is injected through the central orifice. At the outlet of the radial pipes, means are advantageously provided which form baffle plates so as to direct the liquid properly towards the bottom of the cell. For each cell, the effect of centrifuging is to expel via the peripheral orifice the excess compound which has not been fixed onto the solid support.

After washing, drying can optionally be performed by shutting off the washing liquid inlet while continuing centrifuging.

These operations are then repeated with a reagent which has the property of fixing itself onto the beginning of the chain built up during incubation.

After further incubation, removal of the loose excess, washing and drying a geiger counter is used to make a reading in the case where the reagent was marked with an isotope. If marking was done using an enzyme, a calibrated quantity of substrate is added to cause a coloured reaction which is directly read in the cell by a photometer.

The disadvantage of this apparatus, which is otherwise very advantageous, is that to fill each cell with compound and reagents, it is necessary to place the cell in communication with the feed devices concerned, e.g. pipettes which contain said compound and reagents. This limits the degree to which the rotor is self-contained in operation.

An aim of the invention is to provide an analysis apparatus of the above-described type in which the cells are fed with compound and reagent without using pipettes and using means which ensure a more self-contained mode of operation for the analysis apparatus.

SUMMARY OF THE INVENTION

The present invention provides analysis apparatus of the kind which uses a reaction support to hold successively a quantity of a liquid which contains a substance to be analysed and then a quantity of a liquid reagent to react therewith, wherein the apparatus comprises an analysis rotor having: a plurality of peripheral reaction cells each containing a reaction support; means for centrifuging a washing liquid into each reaction cell; a peripheral liquid-removal orifice for each reaction cell; a buffer cell associated with each reaction cell; means for successively centrifuging at least said liquid containing a compound to be analysed and a first reagent into said buffer cell; and means for storing predetermined quantities of said first reagent in sealed receptacles and for opening said receptacles when it is required to centrifuge the first reagent into said buffer cells; the buffer cell reaction cell pairs being so arranged that liquid in the buffer cells moves into the associated reaction cells when centrifying stops.

The invention also provides a method of using analysis apparatus comprising the steps of:

centrifuging the liquid which contains the substance to be analysed into the buffer cells;

stopping rotation to allow said liquid to pour completely into the associated reaction cells;

leaving the liquid to react for a suitable incubation time; removing excess liquid from the reaction cells by centrifuging the rotor, and introducing a washing liquid into the reaction cells to wash their reaction supports;

optionally performing a drying operation by turning off the supply of washing liquid while continuing to centrifuge;

opening said sealed receptacles and centrifuging a first reagent into the buffer cells;

stopping rotation to allow said first reagent to pour completely into the associated reaction cells;

leaving the reagent to react for a suitable period; and removing excess liquid from the reaction cells by centrifuging the rotor, and introducing a washing liquid into the reaction cells to wash their reaction supports; and optionally drying the reaction supports and optionally repeating the steps involving a reagent with a second reagent.

BRIEF DESCRIPTION OF THE DRAWINGS

Two embodiments of the invention are described by way of example, with reference to the accompanying drawings, in which:

FIG. 9 is a partial perspective view of a second embodiment of the invention showing a pair of associated superposed cells;

FIG. 10 is a cross-section passing through cell radial feed pipes showing a pair of associated superposed cells;

FIG. 11 is a cross-section view along line XI—XI of FIG. 10;

MORE DETAILED DESCRIPTION

Figure 1:
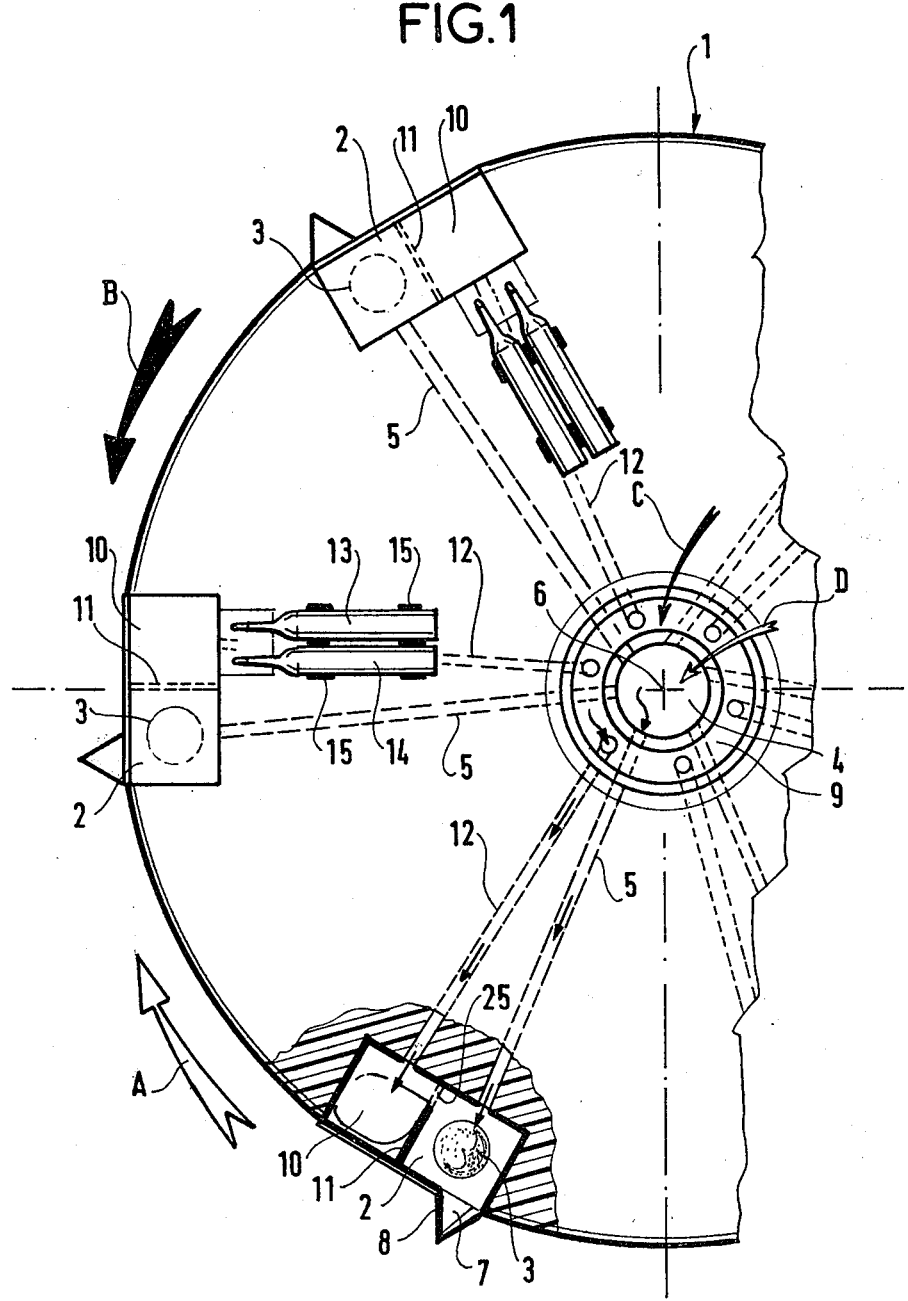
FIG. 1 is a diagrammatic top view of a first embodiment of the invention partially cut away at a pair of associated juxtaposed cells.
Figure 2:
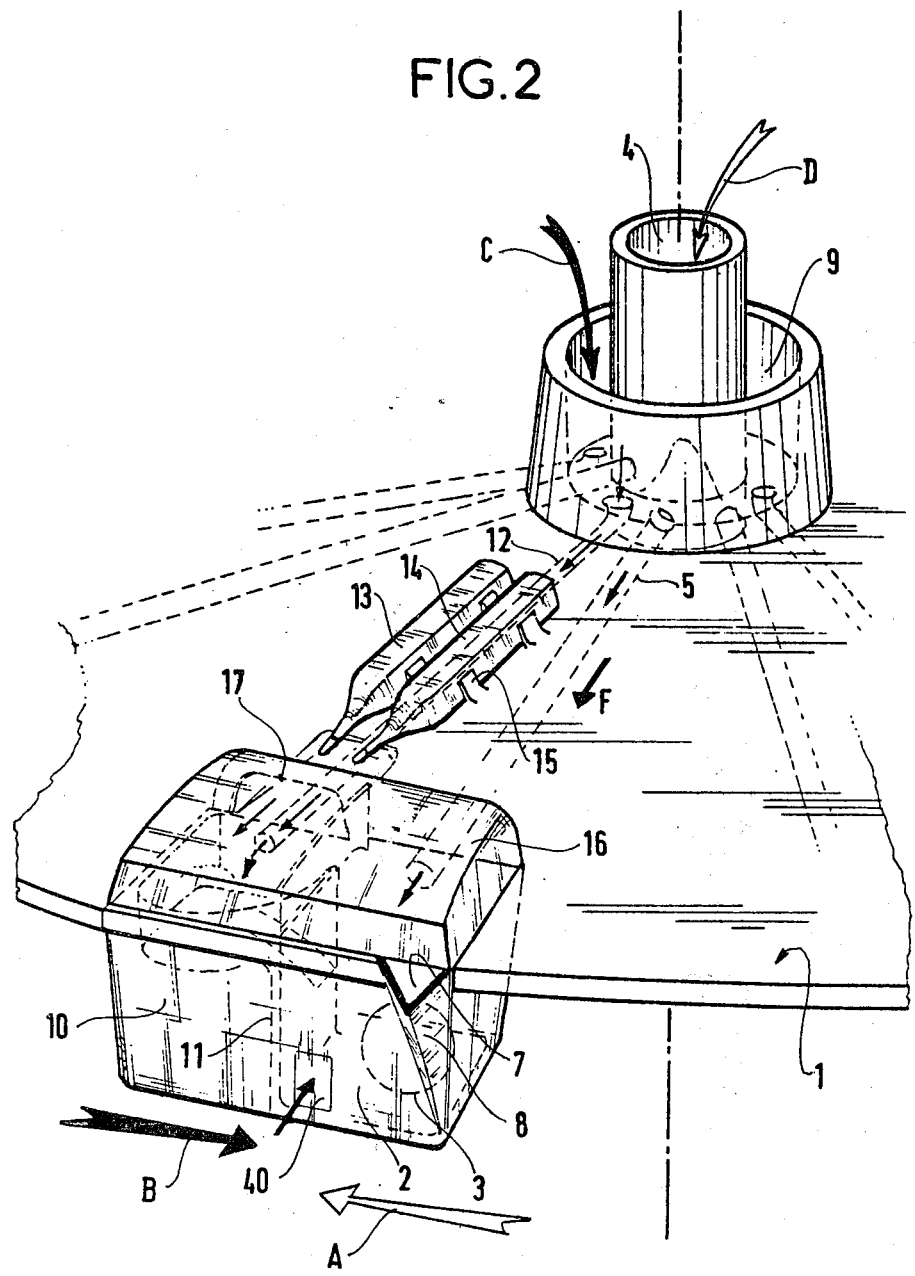
FIG. 2 is a perspective view of part of the embodiment shown FIG. 1.
Figure 3:
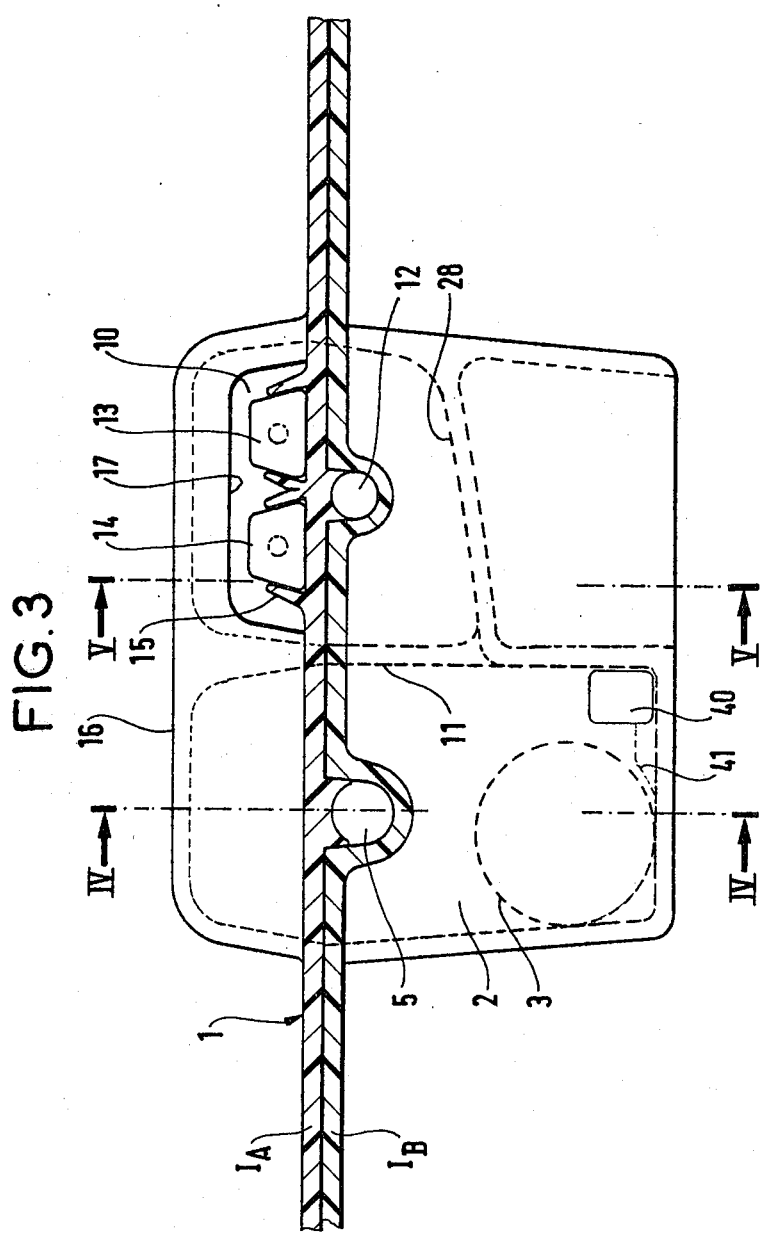
FIG. 3 is an elevation in the direction of an arrow F of FIG. 2.
Figure 4:
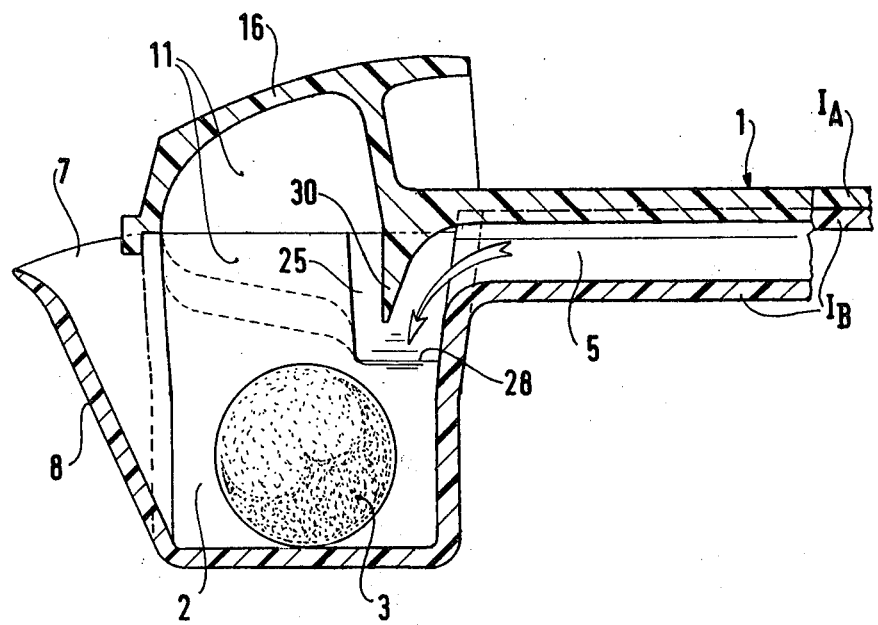
FIG. 4 is a cross-section along line IV—IV of FIG. 3.
Figure 5:
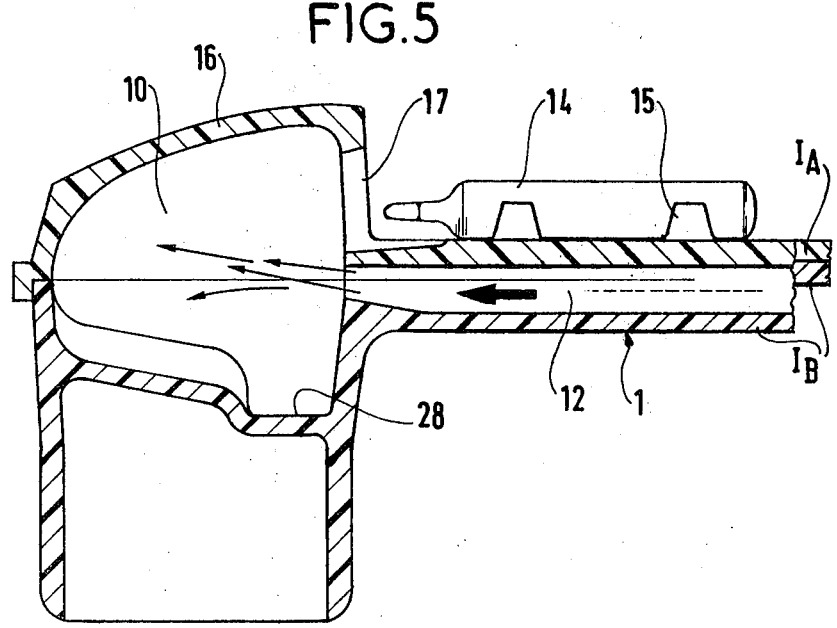
FIG. 5 is a cross-section along V—V of FIG. 3.

The figures show two analysis devices in accordance with the invention. Their main components are a rotor 1 having a plurality of peripheral reaction cells 2, each of which contains a reaction support 3. The rotor 1 is assembled from upper and lower generally disc-shaped members referenced IA and IB for the embodiment of FIGS. 1 to 8 and $I_A$ and $I_C$ for the embodiment of FIGS. 9 to 14.

In the embodiments illustrated, the reaction support is constituted by a single conventional reaction support comprising, for example, a bead of polystyrene covered with a compound having anti-body type properties.

However, instead of a single bead, a plurality of small beads may be used, e.g. with a diameter of about of 10 to 20 microns. In such a case, a barrier would be fitted in the cells suitable for retaining the beads therein while the apparatus is rotating, this barrier being embedded or glued in suitable notches. Advantageously, such a barrier would be of the molecular filter type.

The solid reaction support could also be constituted by a suitable coating deposited on lower portions of the walls of the reaction cells 2.

Reference 4 designates a central inlet orifice for a washing liquid which is let in as shown by an arrow D. Radial pipes 5 leave the central orifice and connect it to each peripheral cell 2. The pipes are disposed in a plane which is essentially perpendicular to the axis of rotation 6 of the apparatus. It should be observed that although the radial pipes 5 are defined in the embodiment shown by two complementary semi-cylindrical portions formed in the upper and lower disc-shaped $I_A$ and $I_B$ members (e.g. see FIGS. 3 and 10), other type of pipe could be envisaged such as, for example, a flat on one portion of the rotor and a groove on the other.

Each reaction cell 2 has a peripheral liquid-removal orifice 7 (constituted by a gap between the outer edges of the upper and lower members $I_A$ and $I_B$). The liquid-removal orifice 7 is at the end of a spout 8 which is itself located at the rear of the reaction cell 2 when the rotor 1 is rotating in the washing direction, symbolised by an arrow A.

Reference 9 designates a circular orifice arranged concentrially around the central inlet orifice 4. The liquid compound which contains the substance to be analysed is introduced into the circular orifice 9 in the direction shown by an arrow C.

Each reaction cell 2 is coupled to a buffer cell 10 (FIGS. 1 to 8) or 10′ (FIGS. 9 to 14) which shares a common wall 11 (FIGS. 1 to 8) or 11′ (FIGS. 9 to 14) with the reaction cell 2 containing the reaction support 3. A passage is provided between cells 2 and 10 or 2 and 10′ to allow liquid to pass around the wall 11 or 11′.

In the case of the embodiment illustrated in FIGS. 1 to 8, the cells 2 and 10 are juxtaposed. The common wall 11 which separates them is a radial wall.

In the case of the embodiment illustrated in FIGS. 9 to 14, the cells 2 and 10′ are superposed, the common wall 11′ being constituted by the upper surface of the reaction cell 2.

The buffer cells 10 and 10′ communicate with the concentric inlet orifice 9 via radial pipes 12.

The ends of these pipes nearest to the buffer cells are provided with capillary constrictions preceded by pockets. These, together with stoppers which can be inserted in the orifice 9 to separate it from said pockets serve to define predetermined volumes.

For simplicity's sake, all this system which is well-known per se and which aims only to bring a well-determined volume of liquid into the buffer cells 10 and 10′ is not illustrated in the drawings.

These radial pipes 12 are likewise defined by complementary portions formed on the members $I_A$, $I_B$ of the rotor in FIGS. 1 to 8 or $I_A$, $I_C$ of the rotor in FIGS. 9 to 14, but any other type of pipe could be envisaged.

The upper surface of the rotor is equipped with means suitable for holding reagent-containing receptacles such as capsules, bulbs, etc. in such a position that, by centrifuging and opening these receptacles, the liquids they contain are introduced into the buffer cells 10 or 10′.

In the embodiment illustrated in FIGS. 1 to 8, the reagent-containing receptacles 13 and 14 are held on the upper surface of the rotor by locking clip supports such as 15. The upper parts of the associated pairs of cells 2 and 10 are closed by covers 16 each of which has an opening 17 facing the openings of the receptacles 13 and 14.

The analysis apparatus is equipped with means, not illustrated, suitable for opening the receptacles 13 and 14 to be opened; these means may act e.g. by radiation, heating or crushing and are well known in the handling of pharmaceutical products.

In the embodiment illustrated in FIG. 9 to 14, the reagent-containing receptacles are held in troughs 18.

Figure 13:
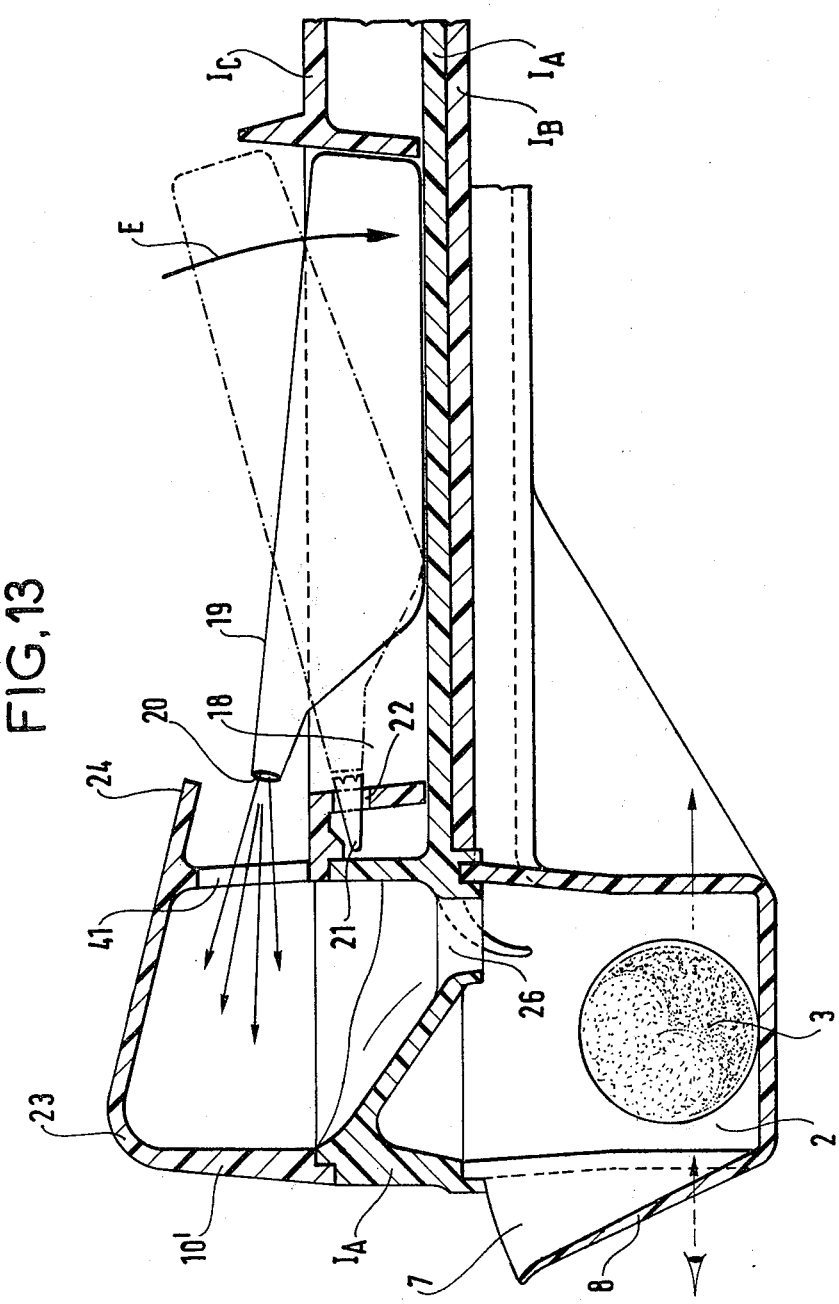
FIG. 13 is a cross-section view of a pair of associated superposed cells along line XIII—XIII of FIG. 9.
Figure 14:
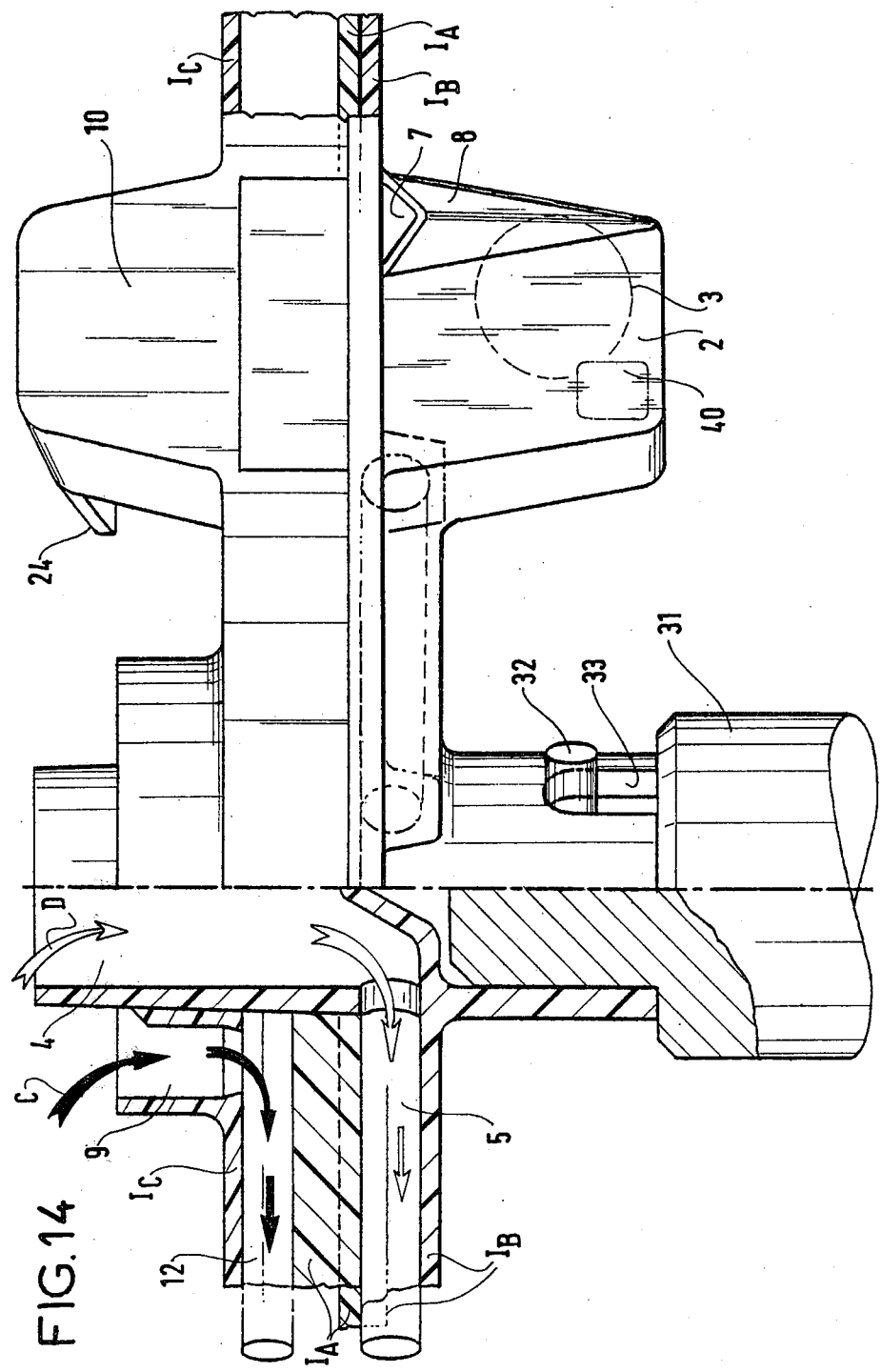
FIG. 14 is a partially cut-away elevation through the central portion of the apparatus.

FIG. 13 illustrates a process for opening such a receptacle 19 whose outlet orifice 20 is situated at the end of an elongated portion 21. Before opening, the end of this elongated portion 21 is engaged in a suitable hole 22 in the radially outer end of the trough 18, in a position such that the receptacle has its radially inner end raised out of the trough 18.

When it is required to open the capsule 19, its raised end is pushed downwards in the direction shown by an arrow E and the elongated portion 21 is broken off, thereby opening the orifice 20. The reagent is expelled through the orifice 20 and then enters the buffer cell 10′ via an opening 41 provided in its cover 23.

The cover 23 has a small lip 24 which overhangs the orifice 21 and ensures that all the liquid expelled from the receptacle 19 actually enters the buffer cell 10′.

Of course, any other suitable means can be used to open the reagent-containing receptacles and to hold said receptacles on the upper surface of the rotor.

The wall which is common to a buffer cell and to a reaction cell has a hole in it which puts the two cells in communication with each other.

The embodiment illustrated in FIGS. 1 to 8 corresponds to the case where this common wall 11 is a radial wall. The hole is therefore located in the upper part thereof on its radially inner side and is in the form of a slot referenced 25.

In the embodiment illustrated in FIGS. 9 to 14 which correspond to the case where the common wall 11 is the upper surface of the cell 2, the hole is referenced 26.

The inside profile of the buffer cells (10 or 10′) is such that all the liquid brought into said cells by centrifuging in direction B is retained therein and cannot escape into the reaction cell 2 until centrifuging is stopped, whereupon all the liquid thus brought into the buffer cell (10 or 10′) passes into the reaction cell 2 via the orifice (25 or 26).

With this aim in view, the orifice 25 is disposed at a level higher than that reached by the liquid in the reaction cell 2 after the quantity retained in the buffer cell 10 has poured away.

Figure 6:
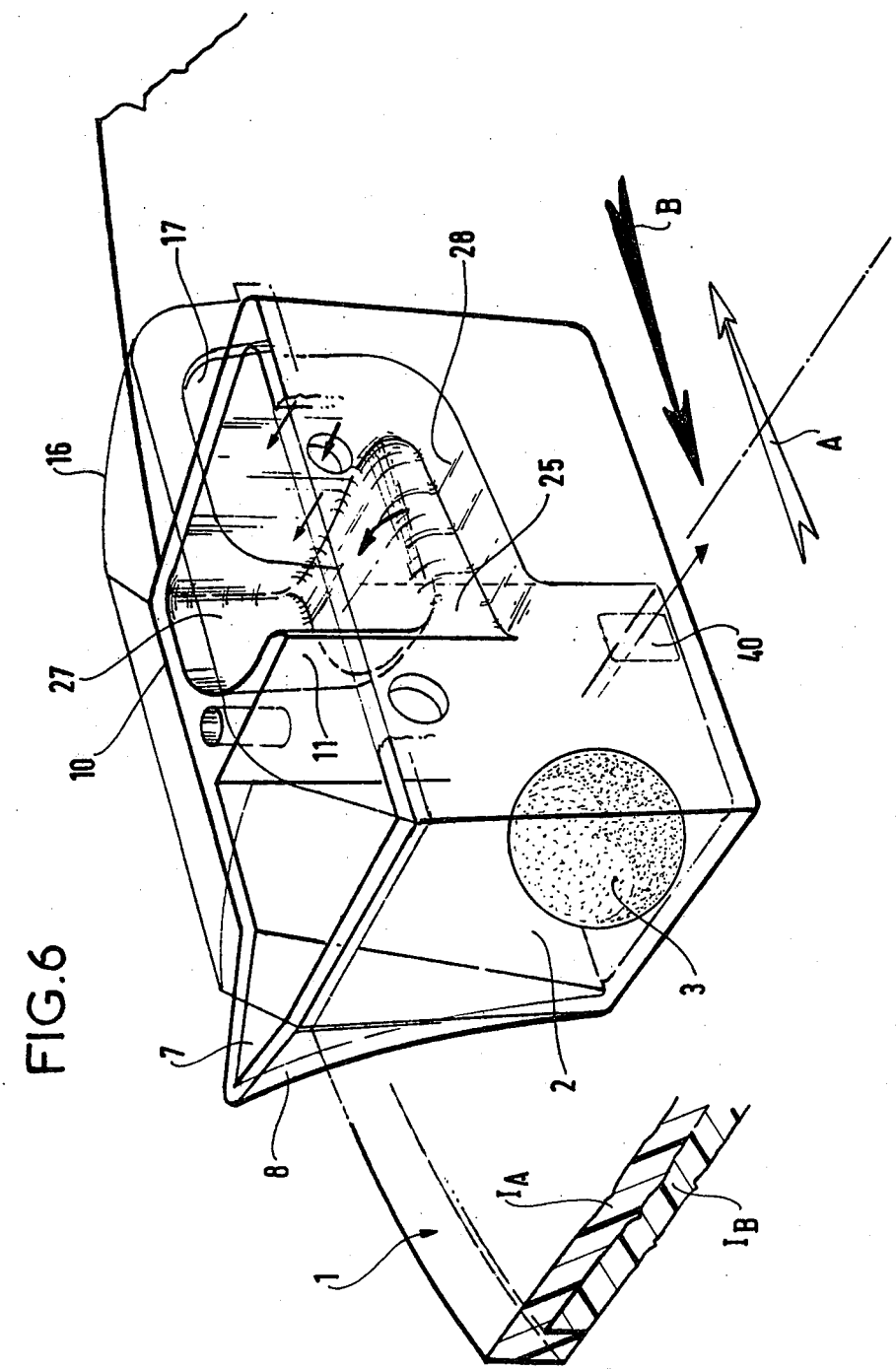
FIG. 6 is a partially cut-away diagrammatic perspective view of a pair of associated juxtaposed cells.
Figure 7:
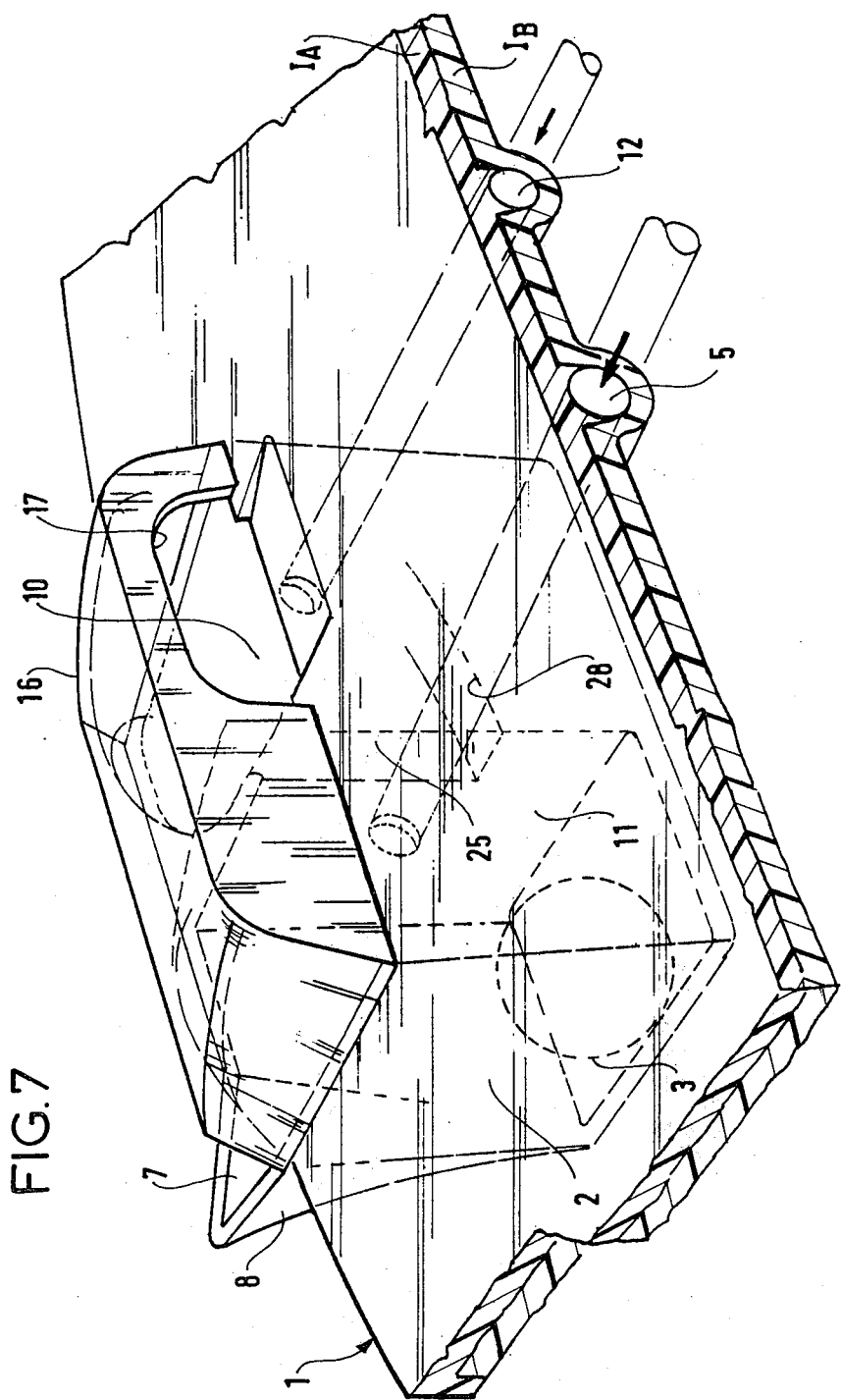
FIG. 7 is a non cut-away view in the same perspective as FIG. 6.
Figure 8:
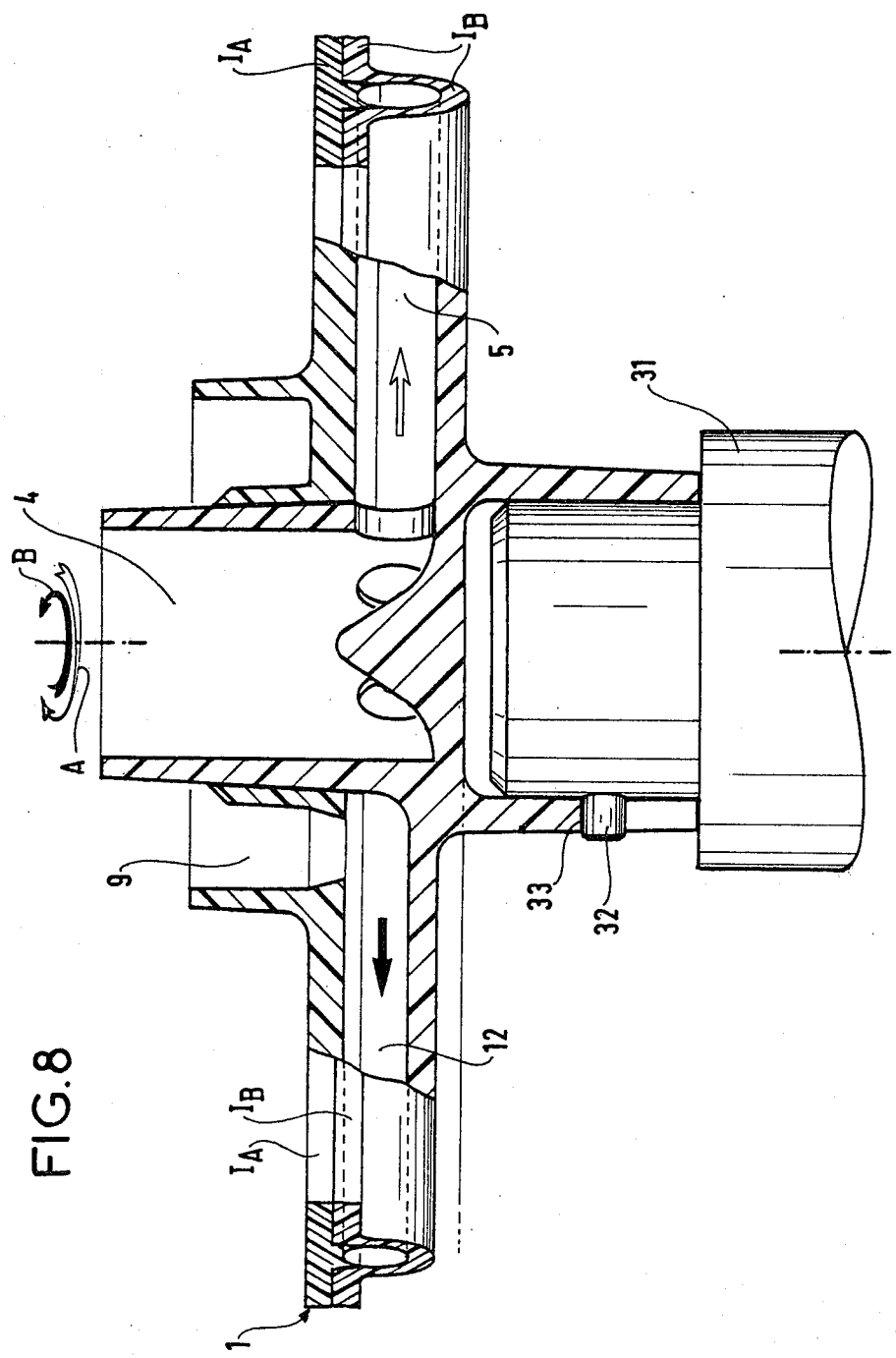
FIG. 8 is a partial cross-section view through the central part of the analysis apparatus.
Figure 12:
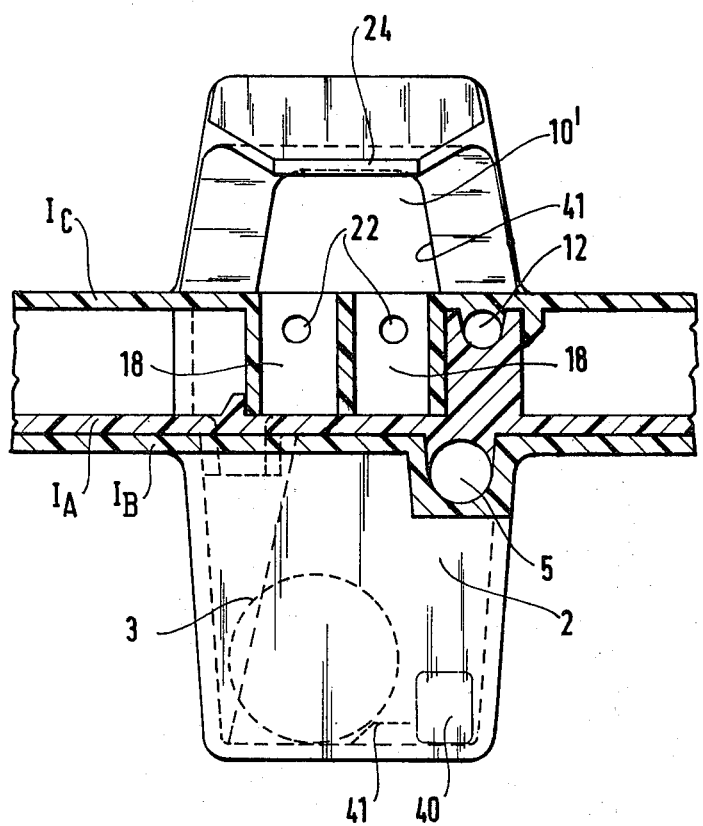
FIG. 12 is a cross-section view along line XII—XII of FIG. 9.

As can be observed in FIG. 6, the buffer cell 10 has a retaining zone 27 near its outer surface. This retaining zone overhangs a removal ramp 28 which leads to the lower level of the orifice 25. Thus, after stopping centrifuging the liquid which was retained in the zone 27 pours into the reaction cell 2 via the ramp 28 and the orifice 25.

The buffer cell 10′, FIG. 10, also has a retaining zone 29 positioned at its rear relative to the direction of rotation (B) used during buffer cell filling operations.

Since the buffer cell 10′ is superposed on top of the reaction cell 2, the liquid it contains pours readily into the reaction cell 2 when centrifuging stops.

To guide the washing liquid properly into the bottom of the reaction cell 2, a baffle plate 30 is provided near the end of the feed pipe 5 which communicates with the cell 2.

The rotor 1 is made to rotate by entirely conventional drive means. Reference 31 designates a rotary shaft which bears a protruding lug 32 engaging in a suitable notch 33 in the rotor.

The apparatus operates as follows:

A liquid such as serum or plasma which contains a substance to be analysed is inserted in the concentric orifice 9.

A determined volume of this liquid is then trapped between the capillary contrictions provided at the ends of the pipes 12 and a stopper which is inserted in the orifice 9.

Then, centrifuging is carried out in the direction B. The liquid containing the substance to be analysed contained in the pipes 12 then moves into the buffer cells (10 or 10′) and it is retained therein for as long as centrifuging continues.

When centrifuging stops, the liquid enters the reaction cells 2 containing the reaction support 3 and is left to stand during the necessary incubation time. It should be observed that each reaction cell 2 has a sufficient volume to contain the bead and the liquid containing the substance to be analysed without the level thereof reaching the pipes 5.

After this reaction phase between antigen and antibody, the excess liquid is expelled by centrifuging in the direction A while injecting a washing liquid, e.g. water, from the central opening 4 via the pipes 5.

This washing liquid thoroughly washes the reaction support and leaves the cell together with the excess liquid containing the substance to be analysed via the orifice 7 situated at the end of the spout 8.

An optional drying step may then be performed by turning off the washing liquid inlet while continuing centrifuging.

A first reagent—e.g. a polyglucoside—contained in one of the receptacles fixed in the upper wall of the rotor is then introduced.

This is done while centrifuging is being carried out in the direction B, and any suitable means (not illustrated and usually employed in conditioning pharmaceutical products as set forth hereinabove) are used to open the orifices of the receptacles concerned. The liquid then leaves the receptacles and enters the buffer cells (10 or 10′) where it is retained for as long as centrifuging continues in the direction B. When the rotating movement stops, the reagent leaves the buffer cells (10 or 10′) and enters the reaction cells 2 where it comes into contact with the reaction support which has been modified by the preceding antigen anti-body reaction.

After further incubation, removal of non-fixed excess, washing and drying, as required by the type of reagent injected, a direct analysis can be made e.g. by using a Geiger counter if the reagent contains radioactive isotopes or by injecting a second reagent such as a substrate which develops a coloured reaction by the same process to enable the enzymatic activity to be measured by means of a colorimeter or of a photometer. Advantageously, to facilitate this type of analysis the inner and outer surfaces of the reaction cells 2 are parallel, at least in the neighborhood of a reading window referenced 40.

In the case where the reaction support is formed by a bead, means such as 41 are provided in the analysis cell to prevent the bead from coming opposite the reading window.

The reaction supports disposed in the various reaction cells may correspond to different analysis which are made simultaneously on the same sample.

By way of an example, the apparatus in accordance with the invention makes it possible to simply and rapidly obtain the five simultaneous dosages required for a thyroid analysis. Flexibility is also illustrated by the possibility among others of dividing the rotor into two zones to use some reaction cells as reference or check cells and of using different supports or identical reaction supports which would make it possible to carry out a single test for different customers.

A compact apparatus can be produced in accordance with the invention. For example, it may have a diameter of about 8 cm.

I claim:

1. Analysis apparatus of the kind which uses a reaction support to hold successively a quantity of a liquid which contains a substance to be analysed and then a quantity of a liquid reagent to react therewith, said apparatus comprising an analysis rotor having: a plurality of peripheral reaction cells each containing a solid reaction support; means for centrifuging a washing liquid directly into each reaction cell; a peripheral liquid-removal orifice for each reaction cell; the improvement comprising:

separate means for successively centrifuging at least said liquid containing a compound to be analysed and a first reagent directly into said buffer cell;

means for storing predetermined quantities of said first reagent in sealed receptacles and for opening said receptacles when it is required to centrifuge the first reagent into said buffer cells;

means for communicating said reaction cells and said buffer cells; and the buffer cell-reaction cell pairs being so arranged that liquid in the buffer cells moves into the associated reaction cells when centrifuging stops.

2. Analysis apparatus according to claim 1, wherein the cells of each pair are juxtaposed, with a common radial wall separating the cells from each other.

3. Analysis apparatus according to claim 1, wherein the cells of each pair are superposed, with a common horizontal wall comprising the upper surface of the reaction cell separating the cells from each other.

4. Analysis apparatus according to claim 1, wherein the internal profile of the buffer cells is such as to ensure that any liquid brought into said cell during centrifuging is unable to escape towards the reaction cell until centrifuging is stopped, and where upon all the liquid brought into the buffer cell passes into the associated reaction cell.

5. Analysis apparatus according to claim 1, wherein the means by which the washing liquid is conveyed comprise a central inlet orifice and radial pipes connecting said central orifice to each of the peripheral reaction cells, respectively.

6. Apparatus according to claim 5, wherein the liquid which contains the substance to be analyzed is applied to the rotor via an orifice which is concentric with the inlet orifice for the washing liquid, radial pipes connecting said orifice to the buffer cells.

7. Apparatus according to claim 6, wherein the end of each radial pipe which leads to the buffer cells has a capillary constriction preceded by a pocket, said constriction together with a shutter insertable into the concentric orifice to separate it from said pockets serving to delimit a predetermined volume.

8. Analysis apparatus according to claim 1, wherein the reaction support is formed by at least one bead.

9. Analysis apparatus according to claim 8, wherein the support is constituted by a plurality of beads of very small dimensions, and a barrier is disposed in each reaction cell adjacent said peripheral liquid-removal orifice and said barrier retaining the beads during centrifuging.

10. Analysis apparatus according to claim 9, wherein said barrier is of the molecular filter type.

11. Apparatus according to claim 9 or 10, wherein the diameter of said beads lies between substantially 10 and 20 microns.

12. Apparatus according to claim 1, wherein the reaction support is constituted by a coating deposited on the lower portion of the wall of each reaction cell.

13. Analysis apparatus according to claim 1, wherein the inner and outer surfaces of the reaction cells are substantially parallel at least at the level of an observation window, the outer surface further having a side spout ending in said liquid removal orifice and allowing the complete removal of the washing liquid during centrifuging.

14. Analysis apparatus according to claim 13, wherein the spout is located at the rear of the reaction cell relative to the direction of rotation used during the washing operation.

* * * * *